US006132470A

United States Patent [19]
Berman

[11] Patent Number: 6,132,470
[45] Date of Patent: Oct. 17, 2000

[54] APPARATUS AND METHOD FOR PROTECTING PROSTHETIC JOINT ASSEMBLY FROM WEAR

[75] Inventor: Andrew B. Berman, Flagstaff, Ariz.

[73] Assignee: W. L. Gore & Associates, Inc., Newark, Del.

[21] Appl. No.: 08/801,402

[22] Filed: Feb. 20, 1997

Related U.S. Application Data

[63] Continuation of application No. 08/388,657, Feb. 14, 1995, abandoned, which is a continuation-in-part of application No. 08/187,572, Jan. 27, 1994, abandoned.

[51] Int. Cl.[7] .................................. A61F 2/36; A61F 2/30
[52] U.S. Cl. ................................ 623/23.15; 623/23.76; 623/926
[58] Field of Search ................................. 623/11, 22, 23, 623/18

[56] References Cited

U.S. PATENT DOCUMENTS

| | | |
|---|---|---|
| 3,286,713 | 11/1966 | Kurtz et al. ............................. 604/180 |
| 3,648,294 | 3/1972 | Shahrestani ........................... 623/18 X |
| 3,683,421 | 8/1972 | Martinie . |
| 3,739,403 | 6/1973 | Nicolle . |
| 3,938,198 | 2/1976 | Kahn et al. . |
| 4,187,390 | 2/1980 | Gore ..................................... 174/102 R |
| 4,357,716 | 11/1982 | Brown . |
| 4,403,604 | 9/1983 | Wilkinson et al. ....................... 600/37 |
| 4,488,549 | 12/1984 | Lee et al. . |
| 4,562,598 | 1/1986 | Kranz . |
| 4,664,669 | 5/1987 | Ohyabu et al. ........................... 623/66 |
| 4,731,088 | 3/1988 | Collier . |
| 4,743,252 | 5/1988 | Martin et al. ............................... 623/1 |
| 4,778,472 | 10/1988 | Homsy et al. . |
| 4,783,192 | 11/1988 | Wroblewski et al. . |
| 4,787,921 | 11/1988 | Shibata et al. ............................... 96/6 |
| 4,816,339 | 3/1989 | Tu et al. ................................. 428/421 |
| 4,822,368 | 4/1989 | Collier . |
| 4,871,366 | 10/1989 | von Recum et al. ..................... 623/11 |
| 4,888,024 | 12/1989 | Powlan . |
| 5,032,445 | 7/1991 | Scantlebury et al. ............ 604/890.1 X |
| 5,147,366 | 9/1992 | Arroyo et al. . |
| 5,380,328 | 1/1995 | Morgan ..................................... 606/70 |
| 5,380,329 | 1/1995 | Elia et al. ................................. 606/72 |
| 5,433,996 | 7/1995 | Kranzler et al. ......................... 428/247 |
| 5,462,781 | 10/1995 | Zukowski ............................... 428/36.1 |
| 5,514,182 | 5/1996 | Shea . |
| 5,700,479 | 12/1997 | Lundgren ............................. 623/11 X |

FOREIGN PATENT DOCUMENTS

| | | |
|---|---|---|
| 0016480 | 10/1980 | European Pat. Off. ................. 623/22 |
| 0320138 | 6/1989 | European Pat. Off. . |
| 0346294 | 12/1989 | European Pat. Off. . |
| 3130732 | 5/1983 | Germany ................................ 623/22 |
| 3741490 | 6/1989 | Germany . |
| 9007308 | 7/1990 | WIPO ..................................... 623/11 |
| 9103993 | 4/1991 | WIPO . |
| 9321858 | 11/1993 | WIPO ..................................... 623/11 |
| 9510990 | 4/1995 | WIPO . |
| 9520369 | 8/1995 | WIPO . |

OTHER PUBLICATIONS

Derbyshire B et al.. Problems of encapsulation of total joint replacements. Biomaterials 1980; 1:33–37.*

*Primary Examiner*—David H. Willse
*Attorney, Agent, or Firm*—Wayne D House

[57] ABSTRACT

The disclosure relates to a tissue and debris barrier for use in association with implanted joint replacement devices. The barrier comprises a biocompatible membrane that is impermeable to debris. The membrane defines an aperture which is positioned about a component of the joint replacement prosthesis. The periphery of the membrane may be mechanically attached by suturing to adjacent tissue. The barrier permits full motion of the replacement joint while preventing or impeding tissue and debris from migrating to and from bone implant interfaces. The preferred barrier material is porous expanded PTFE with one side having a microstructure that promotes tissue attachment and the opposing side having a microstructure that allows highly efficient filtration of fine particulate debris. The barrier may be a single layer material or may be a composite construction in which two or more layers are bonded together.

17 Claims, 5 Drawing Sheets

APPARATUS AND METHOD FOR PROTECTING PROSTHETIC JOINT ASSEMBLY FROM WEAR

CROSS REFERENCE TO RELATED APPLICATION

This application is a continuation of application Ser. No. 08/388,657, filed Feb. 14, 1995, now abandoned, which is a continuation-in-part of application Ser. No. 08/187,572, filed Jan. 27, 1994, now abandoned.

FIELD OF INVENTION

The present invention generally relates to prosthetic joints that are susceptible to the adverse effects of particulate debris and more particularly relates to a barrier which is placed about a portion of the prosthesis or attached to a component of the prosthesis and which barrier will restrict migration of debris to prevent accumulation of debris in areas where bone resorption and impairment of the performance of the prosthesis may result.

BACKGROUND OF THE INVENTION

Total joint replacements are appliances which are surgically implanted to treat advanced stages of joint disease. Generally these appliances are articulating prosthetic devices which in today's medical field are commonly used to replace various joints such as damaged or diseased hips, knees, elbows, wrists and fingers. Most prosthetic joint designs consist of two principal components: (1) a concave socket component; and (2) a generally ball-shaped head which seats in the socket. The socket is usually made from a polymeric material having suitable frictional and biological characteristics such as ultra high molecular weight polyethylene (UHMWPE). The head component articulates in the socket and is usually a suitable metallic material such as stainless steel, titanium or other alloys. The two components are attached or implanted at the articulating bones by a surgical procedure replacing the diseased or damaged joint. The resulting artificial prosthetic joint articulates in a manner closely similar to that of the natural joint. In some cases a partial joint placement occurs and only one component is implanted.

One of the most common procedures of this type is the total hip arthroplasty commonly termed the total hip replacement (THR). The THR procedure involves the implantation of a polymeric cup in the acetabulum. The other component is a spherical ball which is carried on an elongate stem. The ball and stem are typically fabricated from a suitable metal such as stainless steel, titanium or other biologically-acceptable alloys. The stem is implanted in the medullary canal of the proximal end of the femur. The spherical ball fits snugly in the polymeric cup creating an articulating joint.

Most joint replacement components require a very close fit with the bone in order to achieve firm anchorage. This is commonly accomplished by applying bone cement or injecting bone cement into the medullary canal prior to inserting the appliance into the bone. More recently, various porous coatings have been developed to which the bone attaches directly eliminating the need for cement. In either case, the interposition of soft tissue between the implant or cement mantle and the bone will result in compromised fixation of the prosthesis.

Loosening of one or both components of the implants is a major complication associated with prosthetic joint replacements. It is also generally recognized that the debris associated with total joint replacements often cause localized or linear osteolysis resulting in the loosening of the prosthesis. Debris from total hip arthroplasty devices generally fall into three basic categories; polyethylene debris from the acetabular component, polymethylmethacrylate (PMMA) debris associated with implants that have been inserted with cement and metal debris. Polymeric and metallic wear debris results from abrasion as the joint articulates and over time this debris begins to accumulate at the proximal end of the femur. The wear rate may be accelerated if debris from the femoral implant site, for example bone cement particles, migrate upwardly to the articulating surfaces causing third-body abrasion. Large quantities of wear debris accumulating in the soft tissue at the proximal end of the femur cause an inflammatory reaction. The reactive soft tissue can cause resorption of the bone at the proximal end of the femur, especially when debris invades the implant-bone interface. The process accelerates as the debris-laden tissue works its way down the stem of the femoral component into medullary canal. This effect is mediated by the metal itself or by the corrosion or fretting products released by certain metals or metal alloys. The migration of debris is believed due in part to joint fluid which carries the debris both upwardly to the interface of the socket and the ball and downwardly along the stem. Joint fluid penetrates far more extensively than previously believed even in a well-fixed joint component.

There are a number of recent articles in the medical literature dealing with wear debris induced osteolysis. As for example see: Periprosthetic Bone Loss in Total Hip Arthroplasty, *The Journal of Bone and Joint Surgery,* Vol. 74-A, No. 6, July 1992; The Problem in Total Joint Arthroplasty: Aseptic Loosening, *The Journal of Bone and Joint Surgery,* Vol. 75-A, No. 6, June 1993; Mechanism and Clinical Significance of Wear Debris-Induced Osteolysis, *Clinical Orthopaedics and Related Research,* No. 276, March, 1992.

Recent findings (Isolation and Characterization of Debris in Membranes around Total Joint Prostheses, *The Journal of Bone and Joint Surgery,* Vol. 76-A, No. 11, November 1994; Composition and Morphology of Wear Debris in Failed Uncemented Total Hip Replacement, *The Journal of Bone and Joint Surgery,* Vol. 76-B, No. 1, January 1994) suggest that the average wear particle diameter associated with THR is between 0.5 and 0.8 microns with particles ranging down to 0.2 microns in diameter.

Various suggestions for dealing with the problem of wear debris induced osteolysis can be found in the prior art. There has been major emphasis on improving cementing techniques or using alternate fixation methods. Other writers suggest reduction of wear debris should be the primary goal of orthopedic research in the future. Membranous enclosures have also been proposed for use with articulate hip joint replacements which isolate or encapsulate the joint. U.S. Pat. No. 3,683,421 discloses a total hip replacement device that comprises a membrane enclosure attached to both components of the joint replacement encapsulating the articulating portion of the joint replacement thus isolating it from the body. The enclosure is filled with a synthetic lubricant material.

U.S. Pat. No. 3,739,403 discloses a joint replacement comprising an encapsulating membranous enclosure. In this case, an enclosure capsule is provided to prevent tissue from growing into the articulating portion of the joint replacement. The enclosure may have small holes which allow body fluid to pass through the capsule providing joint lubrication.

Thus, while the various approaches suggested above may also serve to limit migration of debris and tissue, several problems are associated with an enclosure which extends around the articulating portion of a joint replacement and which is attached to both components. An enclosure or capsule attached to both components of an articulating joint replacement will decrease flexibility of the joint. Continued long-term flexure of the joint will also limit useful life of the capsule due to fatigue failure of the capsule membrane. Preventing dispersion of wear debris away from the articulating components will increase third-body abrasion leading to earlier failure of one or both components. Further, a capsule will not prevent adjacent soft tissue from migrating to and into bone-implant interfaces. Thus, in view of the foregoing it is apparent that there exists a significant problem of complications as a result of wear debris induced osteolysis. While various approaches can be found or are suggested in the medical and patent literature, these approaches have not found wide acceptance in the medical community.

SUMMARY OF THE INVENTION

Minimization of the adverse effects of debris from joint implants such as total hip arthroplasty may be accomplished by the proper placement of a simple barrier between the source of the unwanted debris and areas where accumulation of the debris would adversely affect the long-term performance of the prosthesis. The barrier is attached to or associated with only one component of the joint prosthesis and does not encapsulate or enclose the articulating portion of the device and is applicable to both partial and total joint replacements. The non-encapsulating barrier of the present invention prevents the migration and accumulation of debris in selective areas while also preventing the advancement of fibrous tissues along bone implant interfaces. The barrier of the present invention is simple and it will remain effective for the lifetime of the joint replacement since the barrier is not subject to repeated flexure and possible fatigue failure.

In accordance with the present invention, a non-encapsulating barrier is provided for use with articulating joint replacement devices. The barrier comprises a biocompatible membrane securable to one component of a joint replacement device such that the articulating portion of the joint replacement is not encapsulated. The barrier of the invention is positioned relative to the joint to impede the migration of harmful debris and tissue to and along the implant-bone interface while allowing unimpaired articulation of the joint replacement. The barrier will also impede the migration of particles of fragmented bone cement away from the implant-bone interface.

In accordance with the preferred embodiment of the present invention for use with a total hip replacement prosthesis, the barrier is in the form of a flexible skirt-like membrane which defines an aperture. The neck of the femoral component of the THR extends through the aperture securing the barrier to the prosthesis. In the area of the aperture, the barrier may be formed having an elongated tubular neck or collar which facilitates attachment to the femoral component. The periphery of the barrier extends to cover the opening into the medullary canal and the barrier is suturable to allow initial suture fixation to periosteum or joint capsule tissue.

In my co-pending application, the barrier material is a biocompatible, medically acceptable microporous membrane material which is impermeable to tissue and debris and which also allows long-term fixation of the barrier device by tissue attachment onto the surface of the barrier. Microporous membranes with a pore size of about 10 to 40 microns are preferred for good tissue attachment. An example for a suitable material is a 0.3 mm to 2.0 mm thick porous expanded polytetrafluoroethylene (PTFE) such as that commercially available and designated GORE-TEX® Cardiovascular Patch available from W. L. Gore and Associates, Inc., Flagstaff, Ariz. The two opposing surfaces of the material have a microstructure consisting of nodes and fibrils with a mean fibril length of about 22 microns which promotes tissue ingrowth. This membrane was found to be sufficient for filtration of particles ranging down to about 0.5 microns in diameter. As previously discussed however, wear particles are now thought to range down to 0.2 microns in diameter.

It has been found that a barrier having a laminate structure works particularly well in the presence of particles ranging in diameter down to 0.2 microns. The opposing surface layers of a preferred laminate has a node and fibril microstructure with a mean fibril length of from about 10 to 40 microns which promotes tissue ingrowth. Interposed between these surface layers is a thin (approximately 20 microns) layer of porous expanded PTFE having a mean fibril length of less than about 3 microns. This intermediate layer serves as a highly efficient particle filter while permitting body fluids to pass. The barrier may also be a two-layer laminate. In the two-layer structure, one layer is the tissue ingrowth side and the opposing layer provides highly efficient filtration.

Accordingly, both single layer and composite multiple layer barriers may be fabricated which exhibit the proper biological characteristics being flexible and which impede or resist passage of tissue and debris and also promote tissue ingrowth. The term "membrane" or "material" is used herein to broadly describe materials having these characteristics.

BRIEF DESCRIPTION OF THE DRAWINGS

Throughout the drawings, the same or similar elements have been designated by the same numeral with a letter appended for differentiation among the several embodiments.

DETAILED DESCRIPTION OF THE PREFERRED EMBODIMENTS

Figure 1:
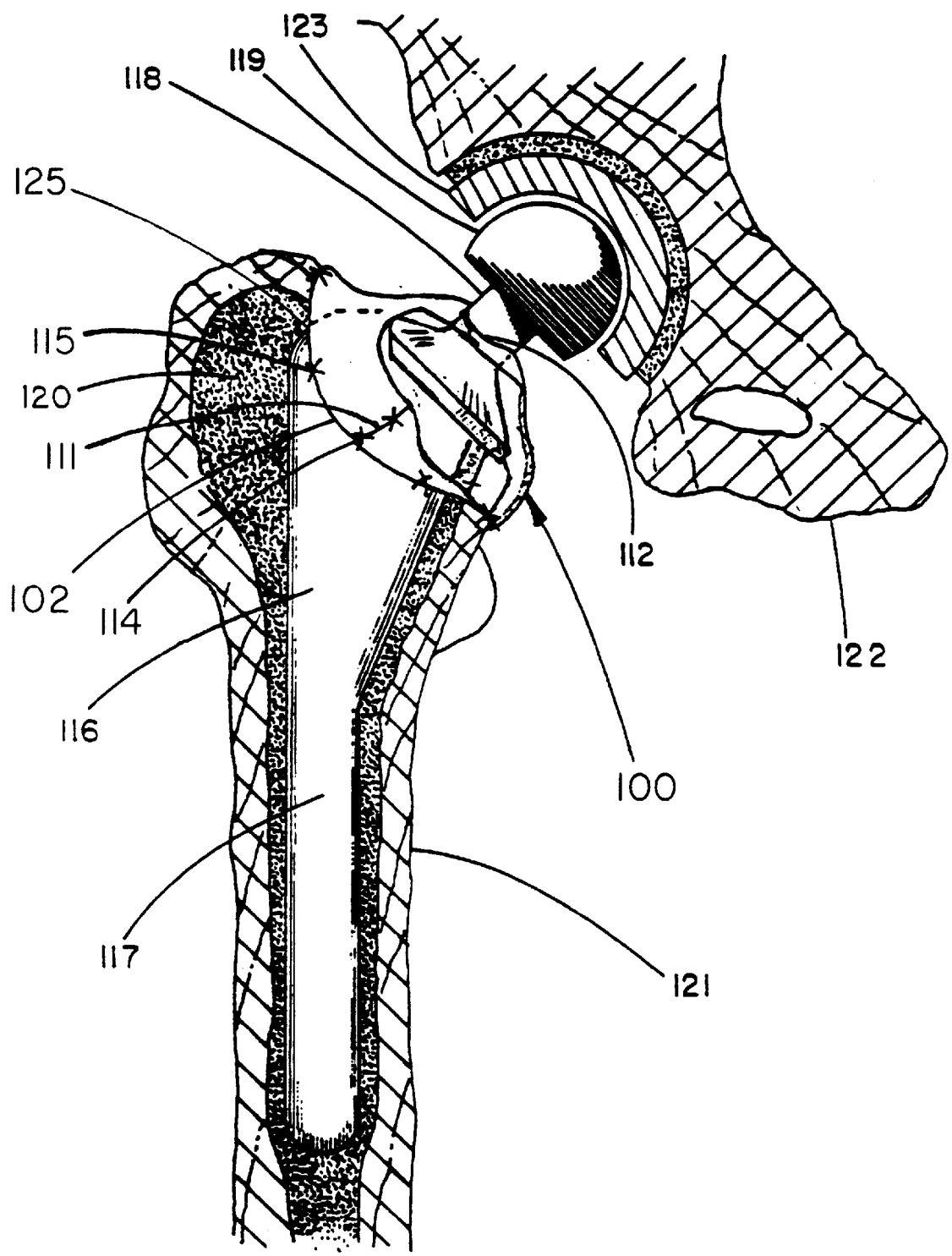
FIG. 1 is a view partly in section illustrating a preferred embodiment of the novel barrier of the present invention shown in conjunction with the hip joint replacement with a portion of the barrier broken away for clarity.
Figure 2:
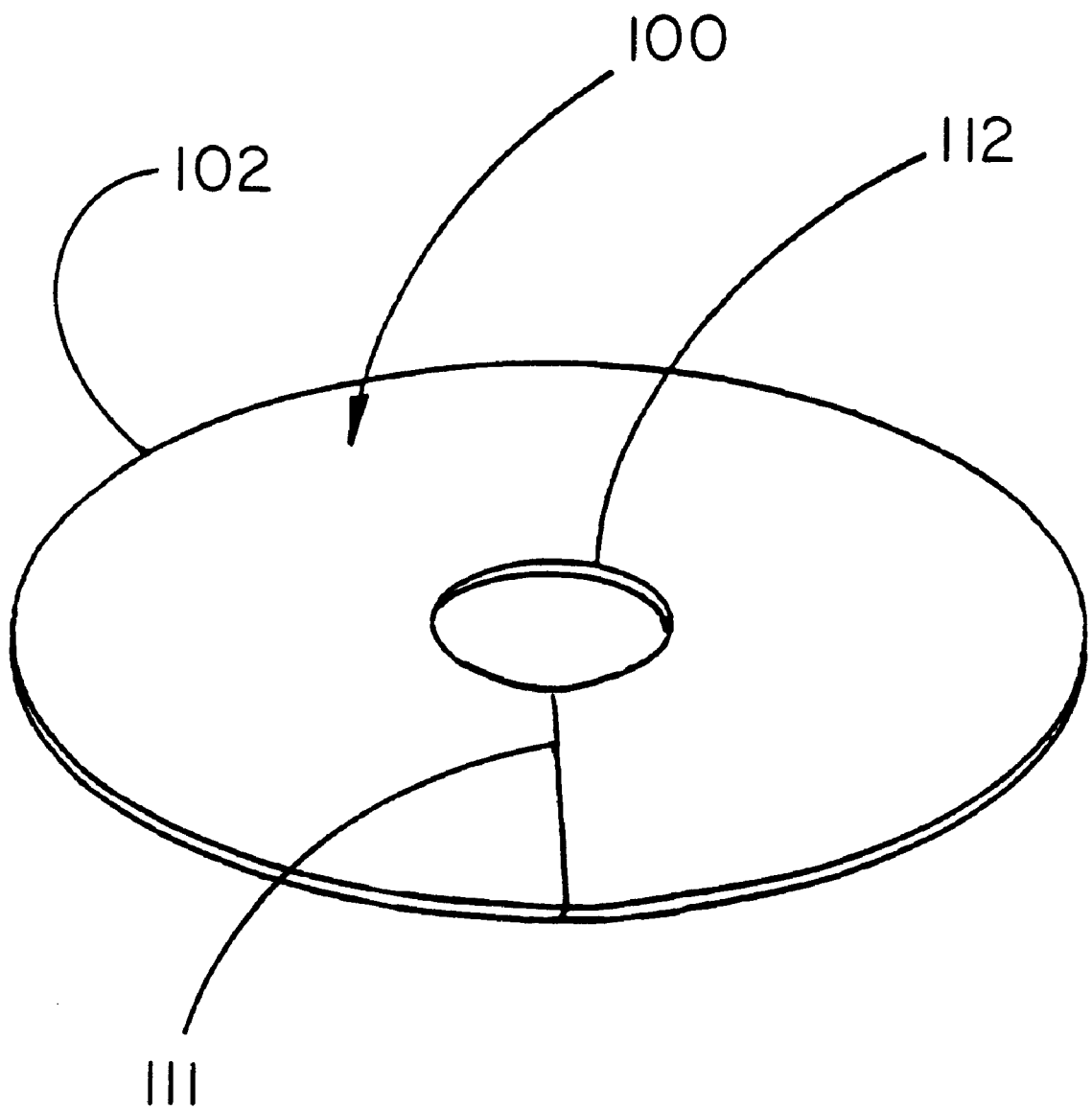
FIG. 2 is a perspective view of the barrier shown in FIG. 1.

Turning to FIGS. 1 and 2, the preferred embodiment of the present invention is shown and is generally designated by the numeral 100. The barrier is shown in connection with a conventional total hip replacement of the integral type. It should be appreciated that the present invention while shown in connection with a THR may be used with any articulating type of joint replacement such as joints for the knee, shoulder, elbow, wrist or finger and may also be used with a partial joint replacement. The construction of the barrier for these various types of joints and the operation and function of the barrier will be substantially the same. The description with respect to the total hip joint replacement is for purposes of understanding only and is not intended to limit the scope of the invention. As indicated, it is understood that the barrier and its function remains the same in the other physical environments having an artificial joint with two relatively rigid intramedullary components interconnected by a flexible or hinge connection to allow articulation. The barrier may also be utilized with a partial joint replacement and attached to the one implanted component.

The hip replacement device as shown in FIG. 1 comprises two principal components, the femoral component 116 and the acetabular component 123. The femoral component has a smooth generally spherical head 119 attached to a neck 118. An elongate shaft 117 is implanted in the proximal end of the medullary canal of the femur 121 and secured in place by application of cement 120. Alternate attachment methods such as porous coatings to promote bone ingrowth may also be used instead of cement. The acetabular component 123 is implanted into hip 122.

In the surgery, a general anesthesia is used and the head of the femur is removed and an opening 125 is provided in the medullary canal. The prosthesis is attached to the femur by inserting the shaft 117 into the canal opening and the acetabulum is implanted. PMMA cement 120 is normally injected into the canal opening 125 prior to insertion of the shaft 117. After a period of therapy, the patients generally obtain substantially full functional motion of the hip joint. The problem of wear debris results from articulation at the interface of the ball head and the acetabular component. Metal and polyethylene wear debris are liberated from this area and are free to migrate. In a cemented prosthesis, cement particles may be released from the interface of the prosthesis and the femur. The problems resulting from the release of debris have been discussed in detail above.

In accordance with the present invention, a barrier 100 is associated with one component of the prosthesis, in this case the femoral component 116. The barrier is a membrane and is a single sheet or a composite fabricated from a biocompatible material that is impermeable to tissue and which is preferably a microporous membrane. A preferred material is porous, expanded PTFE such as GORE-TEX® DualMesh™ Biomaterial, available from W. L. Gore and Associates, Inc., Flagstaff, Ariz., which can be fabricated to have desired characteristics of permeability and tissue growth supporting structure. Porous, expanded PTFE is the preferred material because of its biocompatibility and the variety of microstructures that are possible.

In general, porous, expanded PTFE made per U.S. Pat. Nos. 3,953,566 and 4,187,390 has a microstructure that can be generally characterized as having nodes connected by fibrils.

The porosity of porous, expanded PTFE may be characterized in terms of mean fibril length. The mean fibril length of porous expanded PTFE that has been expanded in a single direction is defined herein as the average of ten measurements between nodes connected by fibrils in the direction of expansion. Ten measurements are made in the following manner: First, a photomicrograph is made of a representative portion of the sample surface, of adequate magnification to show at least five sequential fibrils within a length of the photomicrograph. Two parallel lines are drawn across the length of the photomicrograph so as to divide the photograph into three equal areas, with the lines being drawn in the direction of expansion and parallel to the direction of orientation of the fibrils. Measuring from left to right, five measurements of fibril length are made along the top line in the photograph beginning with the first node to intersect the line near the left edge of the photograph and continuing with consecutive nodes intersecting the line. Five more measurements are made along the other line from right to left beginning with the first node to intersect the line on the right side of the photograph. The ten measurements obtained by this method are averaged to obtain the mean fibril length of the material. For a porous, expanded PTFE material that has been expanded in more than one direction, the mean fibril length is estimated by examining a representative scanning electron photomicrograph of the material surface and comparing fibril lengths as described above in a manner that represents the various directional orientations of the fibrils.

The barrier has sufficient flexibility to conform to the configuration of the surgically modified femur. The outer edge 102 of the barrier defines a suitable geometrical shape which is shown as circular although other shapes such as elliptical or even irregular shapes may be suitable for some applications. The particular peripheral configuration depends somewhat on the particular joint application to which the barrier is to be applied.

The barrier defines an aperture 112 which in this case is shown as a generally circular hole centrally positioned in the barrier. In some applications, the aperture 112 may take various other shapes and may be variously located on the body of the barrier again depending on the particular application and the configuration of the prosthesis with which the barrier is to be used.

A generally radial slit 111 extends from the aperture 112 to the edge 102 of the barrier. In applying the barrier, the surgeon positions the barrier as shown in FIG. 1 once the hip replacement components are in place. The slit 111 in the barrier facilitates placement of the barrier allowing the barrier to be slipped over the head 119 and positioned around the neck 118 of the femoral joint component. Once in this position, the opposite edges of slit 111 are then overlapped or abutted and closure fasteners 114 such as sutures are placed along slit 111 to close the barrier around the neck 118 of the femoral component. The surgeon can ensure that when in position the aperture 112 of the barrier fits snugly around the neck 118 of the prosthesis.

The edge 102 of the barrier is suitably fastened to the periosteum or joint capsule tissue on the femur by sutures 115. The edge of the barrier should extend over the opening 125 in the end of the femur which was surgically modified to accommodate insertion of the femoral component of the prosthesis. Once in place, it will be seen that the barrier will effectively prevent migration of cement particles upwardly along the interface of the shaft 117 and the femur as these particles will encounter the underside of the barrier. Similarly, migration of metal and polymeric particles released from the interface of the ball 119 and the acetabular socket 123 will be impeded and prevented from entering into the interface area between the stem and the femur.

Figure 3:
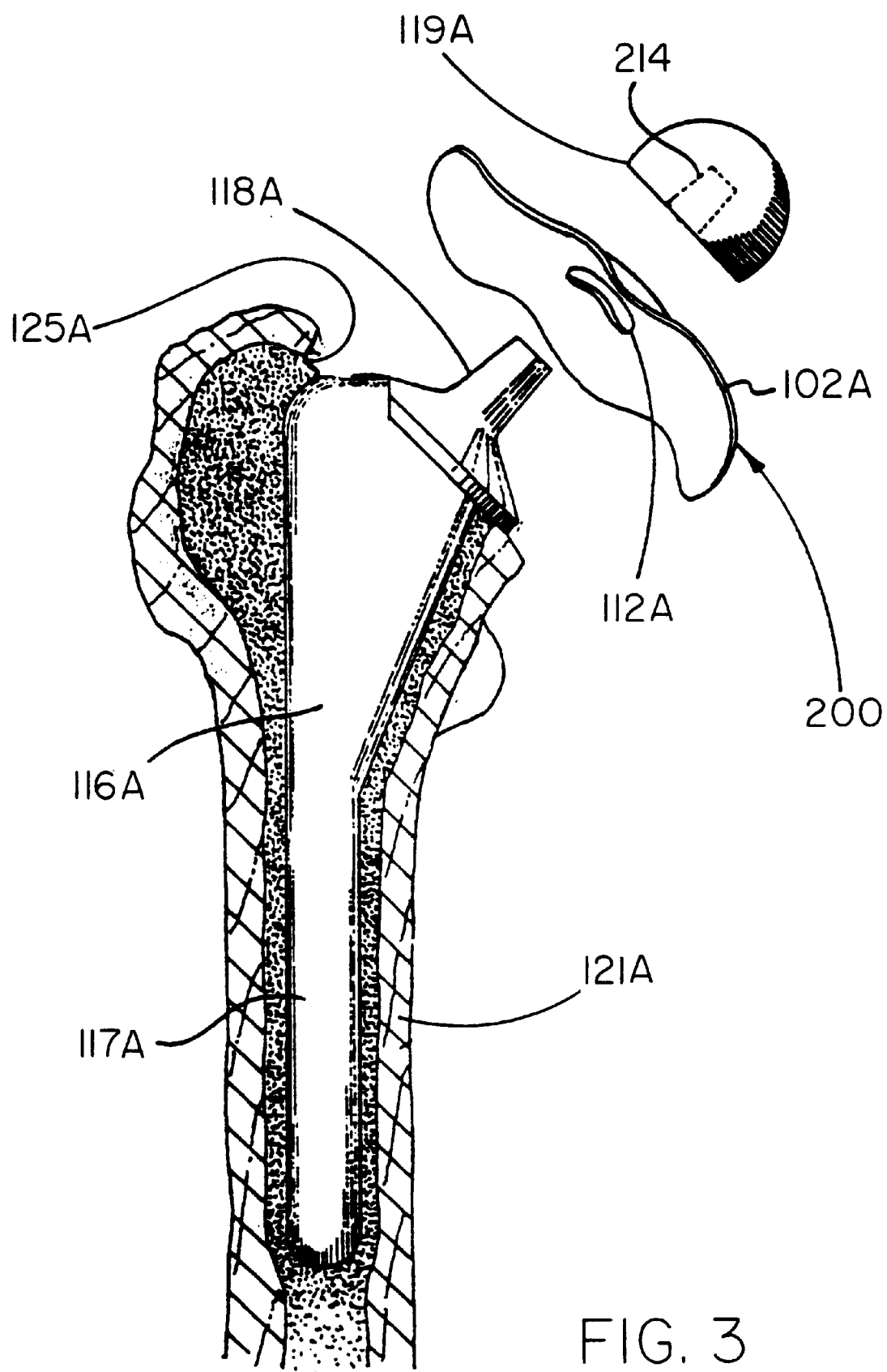
FIG. 3 is a view of another embodiment of the barrier of the present invention shown in conjunction with a modular hip joint replacement device.

FIG. 3, illustrates another embodiment of the barrier of the present invention. The barrier is generally designated 200 and is shown in connection with a modular type of prosthesis device. The modular prosthesis device is shown as a total hip replacement device having a femoral component 116A having a generally elongate shaft 117A which is inserted into the medullary canal of the femur 121A after surgical preparation. Whereas the prosthesis of FIG. 1 is shown as an integral unit, the prosthesis unit of FIG. 3 is modular. The upper end of the femoral stem is provided with a neck 118A which is slightly tapered. The head 119A seats in the acetabular cup (not shown) and defines a tapered bore 214 which receives the distal end of tapered neck 118A in an interference fit when the femoral component is assembled. The barrier 200 again is a membrane fabricated from a suitable biocompatible material as previously described. The barrier is generally flexible having an outer edge 102A and is shown as being circular but may be other geometric shapes depending on the particular application. An aperture 112A has a size which is selected to provide a snug fit when seated on the tapered neck 118A of the component 116A. Prior to positioning the head 119A on stem 118A, the barrier 200 is positioned over the tapered stem 118A. Thereafter the head can be fitted on to the tapered neck completing the prosthesis and securing the barrier in place. Again, the barrier is configured to cover at least the area of the opening 125A that is formed in the head of the femur 121A. Materials for the barrier such as those described above have some elasticity so that the aperture 112A will stretch to snugly fit various sized and shaped prosthesis components. The periphery of the barrier is secured to the femur by suitable sutures.

FIG. 3 also illustrates the application of the barrier to a partial joint replacement. In the event the replacement involves only one component, such as the femoral component, the barrier may be on or associated with the one component as shown in FIG. 3.

Figure 4:
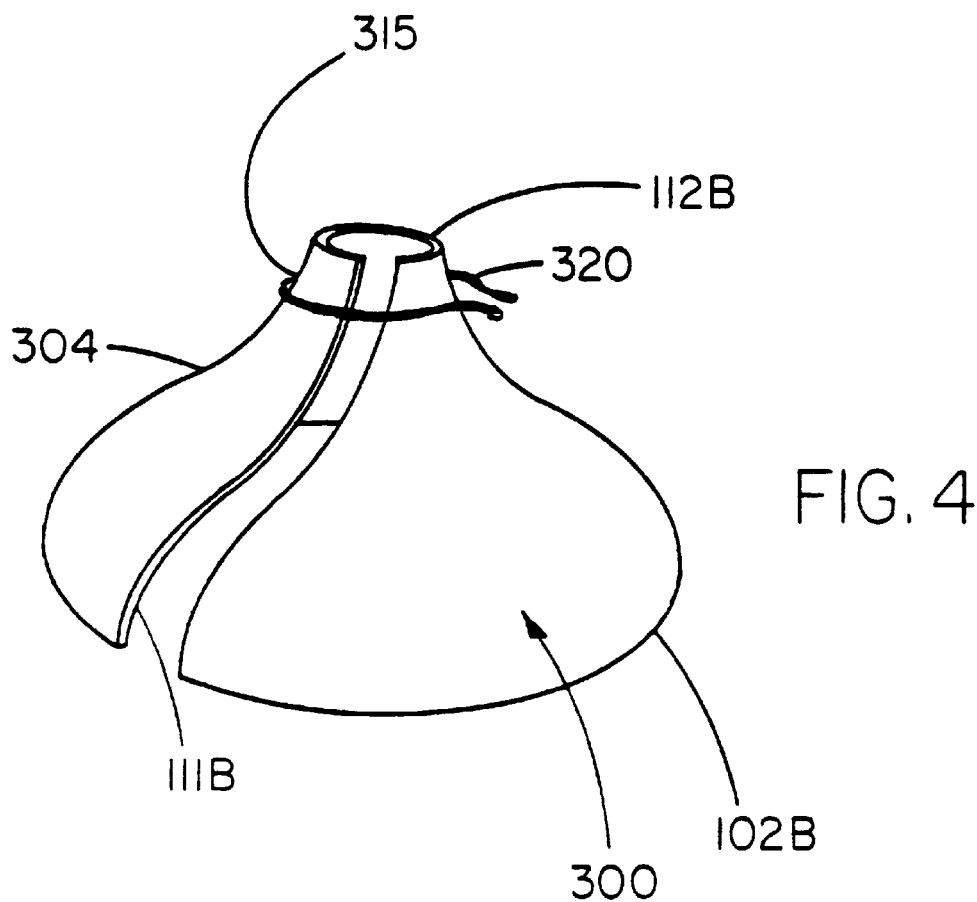
FIG. 4 is a perspective view of still another embodiment of the present invention.

FIG. 4 shows another preferred embodiment of the barrier of the present invention which is generally designated by the numeral 300. The barrier again is fabricated from a microporous membrane material which is preformed having a suitable size and configuration for the particular joint application. The barrier has a peripheral edge 102B which is shown as generally circular, but may be other shapes consistent with a particular application. The barrier has body 304 which is preformed into generally convex shape such as a domed or perhaps slightly conical configuration. The material of the barrier allows the barrier to be preformed into the desired shape by various techniques such as thermoforming, vacuum forming, casting or molding as is appropriate for the selected barrier material.

The upper portion of the barrier is formed into a neck 315 which defines an aperture 112B which is shown as being generally circular. A slit 111B is formed in the surface of the barrier extending from the aperture 112B to the edge 102B of the barrier which facilitates attachment of the barrier to a component of the joint replacement prosthesis. When the barrier is placed about the prosthesis in the manner described above, the opposite edges of slit 111B are abutted or overlapped and closed by suitable mechanical means such as by application of sutures. The edge 102B is sutured to the periosteum or joint capsule tissue on the femur to cover the opening made into the femur. Suitable closure means may be used such as sutures, tape or surgical wire 320 may be wrapped around the neck 315 and secured to tightly seal the barrier around the joint replacement component to which it is secured.

Figure 5:
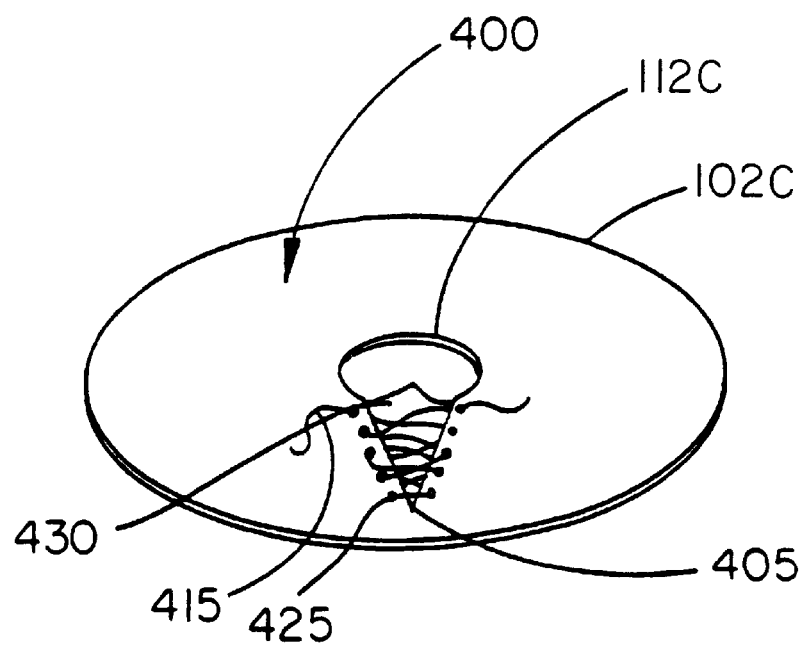
FIG. 5 is a perspective view illustrating yet another embodiment of the novel barrier of the present invention.

FIG. 5 illustrates still another embodiment of the invention which is generally designated by the numeral 400. In this embodiment, the barrier may be die cut or stamped or otherwise formed from a sheet of suitable biocompatible material as has been described. The barrier has an edge 102C which defines a suitable geometric shape and which is for purposes of illustration shown as circular. An aperture 112C is defined at a suitable location generally centrally positioned. The V or wedge-shaped cut 405 extends from the aperture partway to the edge of the barrier to allow suitable expansion of the aperture 112 to facilitate placement on a component of the joint replacement prosthesis. A plurality of holes 425 extend along the opposite edges of the cut 405 through which pre-attached lace or the 415 extends. The tie has opposite free ends to which tension can be applied to when the barrier is positioned about the component of the prosthesis. Closure of the cut 405 by pulling on the laces will cause the barrier to assume a general conical shape. The laces are made of a suitable suture material such as GORE-TEX® Suture Material available from W. L. Gore and Associates, Inc., Flagstaff, Ariz. A flexible pleat 430 of membrane material may be provided extending across the wedge cut 405 on the underside of the barrier to provide further integrity to the barrier when in place.

The foregoing describes the configuration or shape of the barrier. As mentioned, the barrier is fabricated from a membrane which is preferably of porous expanded PTFE. A previously mentioned suitable single-layer membrane is designated as the GORE-TEX® Cardiovascular Patch. A preferred PTFE membrane is of the type designated GORE-TEX® DualMesh™ Biomaterial. This material has opposing surfaces with different characteristics. One surface of this product has a mean fibril length of about 22 microns, while the opposite surface has a mean fibril length of less than about 3 microns. Porous expanded PTFE having the desired characteristics as a barrier material will have one surface with a mean fibril length of about between 10–40 microns with 22 microns being preferred. The opposite surface has a microstructure with a fibril length averaging less than about 3 microns. Thus, one surface will promote tissue ingrowth while the opposite surface will serve as a highly efficient filter generally impervious to the passage of tissue and debris.

Figure 6:
FIG. 6 is a cross-sectional view of a two layer barrier construction.

Referring to FIG. 6, a composite barrier structure designated by the numeral 600 is shown which is a laminate construction consisting of a layer 602 and layer 604. The layer 602 has a microstructure which promotes ingrowth and layer 604 has a microstructure which is a highly efficient filter to small particles. In FIG. 6, the barrier has a total thickness of approximately in the range of 0.3 mm to as much as 2 mm thick with about 0.7 mm being considered a preferred thickness. Layer 602 has a node and fibril porous expanded PTFE structure with a mean fibril length generally in the range of 10 microns to 40 microns with 22 microns being preferred.

Layer 604 has a microstructure with a mean fibril length of less than about 3 microns and acts as a highly efficient filter while being permeable to fluids. The layers comprising the laminate may be adhered together in any suitable fashion that causes them to be adhered during normal intended use. A more detailed description of both a two and three layer fabrication technique is set forth below. This composite configuration provides high filtration efficiency and allows tissue ingrowth on only one surface.

Figure 7:
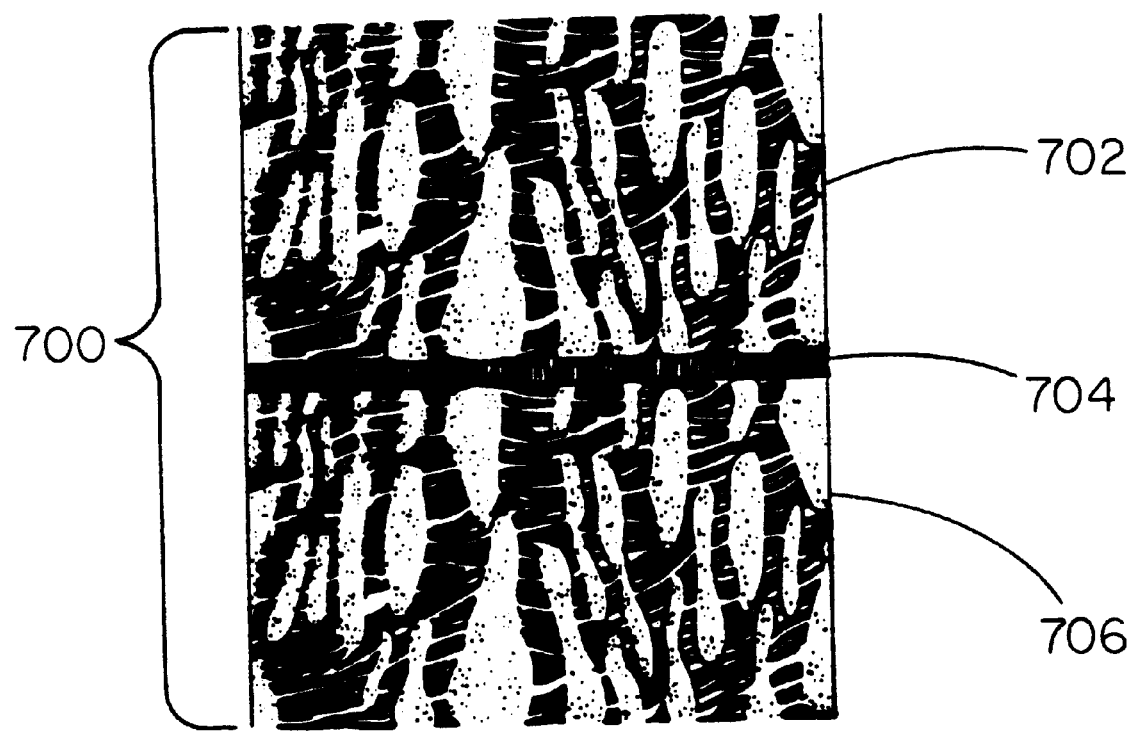
FIG. 7 is a cross-sectional view of a three layer barrier construction.

It is desirable in many instances to promote tissue attachment on both surfaces of the barrier. In this case, a construction as shown in FIG. 7, is preferred in which the barrier is indicated by the numeral 700. Again, the preferred membrane is about 0.7 mm thick but can be manufactured in the range of about 0.3 mm to as much as 2 mm thickness. The two opposing layers, 702 and 706 of the barrier preferably comprise a node and fibril porous expanded PTFE structure with a mean fibril length of between 10 to 40 microns to allow the ingrowth of tissue. Interposed between these surfaces is a thin, approximately 20 micron thick, layer 704 of porous expanded PTFE with a mean fibril length of less than about 3 microns. This intermediate layer 704 acts as a highly efficient filter while being permeable to body fluids. Thus, the three layer composite barrier construction has the advantage of allowing tissue ingrowth on both surfaces while maintaining effective filtration characteristics.

The three layer composite barrier construction as seen in FIG. 7, is fabricated by assembling a stack of extruded and worked PTFE layers in preparation for the expansion operation. The extrusions are made from a paste of PTFE fine powder and a liquid lubricant and extruded in sheet form. The assembly consists of a middle layer of PTFE that has undergone extensive work by means of extrusion and, calendaring followed by drying and expansion. This layer of highly worked PTFE is placed between two or more layers of PTFE that have undergone much less work via extrusion, stretching, and drying. The assembled stack is then compressed between two flat, heated platens to a density near or at that of full density PTFE, i.e. about 2.2 g/cc. The platens are heated to a temperature below the crystalline melt point of PTFE typically 327° C. The compressed laminate structure is then expanded biaxially or radially at or below the crystalline melt point of PTFE typically 327° C. and at an expansion rate that results in a mean fibril length in the range of about 10 to 40 microns with about 22 microns being preferred. The resulting mean fibril length of the particle barrier layer is less than 3 microns. The expansion rate can vary depending upon the amount of work the precursor material has undergone. The material is then sintered at a temperature at or above the melt point of PTFE, approximately 327° C., which cohesively bonds the layers together. The dual layer construction shown in FIG. 6 would be fabricated by a similar fabrication technique as described above wherein the highly worked layer is not interposed between the less worked layers, rather it is placed on top of the stack. This would result in a construction having tissue ingrowth characteristics only at one surface.

Characterization of a single or two-layer material may be performed by using light or scanning electron microscopy as previously described for determination of fibril length. A three-layer material can be characterized by first peeling apart the layers and then using light or scanning electron microscopy to measure fibril length or pore size. If the layer-to-layer bond is too strong to allow peeling, a bubble point pressure test may be performed to characterize the bulk properties of the laminate. A standard procedure known as ASTM F316-86 Method A: Standard Test Method for Pore Size Characteristics of Membrane Filters by Bubble Point may be used. This bubble point test entails first wetting out the test sample in this case with isopropanol, mounting in a fixture, and measuring the amount of air pressure required to force bubbles through the membrane. The bubble point pressure correlates to the effective pore size of the membrane.

EXAMPLE

A single-layer membrane, GORE-TEX® Cardiovascular Patch and a three-layer membrane as described above were characterized using both scanning electron microscopy and ASTM F316-86 Method A with isopropanol as the wetting agent. The surface structure of both membranes had a mean fibril length of about 22 microns. Bubble point testing revealed that the bubble point pressure of the single-layer membrane was about 0.21 to 0.28 kg/cm$^2$. The bubble point pressure of the three-layer membrane was about 2.1 kg/cm$^2$, nearly ten times higher.

To compare the filtration efficiency, both the single layer membrane and the three-layer membrane as described above were challenged with a solution of consisting of $3.00 \times 10^{12}$ 0.2 micron diameter polystyrene latex spheres mixed in deionized water to a concentration of $12 \times 10^{10}$ particles per ml. The challenge solution was pressurized to 0.42 kg/cm$^2$ and the effluent or filtered solution was collected. Turbidometer measurements of the challenge solutions and of the effluent solution were taken. Efficiency of the membrane was calculated as:

$$E = (1 - (\text{effluent} - \text{background})/\text{challenge}) \times 100\%$$

where E=filtration efficiency of the test sample;
Effluent=turbidity of the effluent sample;
Background=turbidity of the background sample;
Challenge=the turbidity of the challenge solution.

The single layer membrane was 85% efficient in filtering 0.2 micron particles. The laminated barrier was 99.85% efficient in filtering the 0.2 micron particles; this result is statistically equivalent to 100% efficient.

From the foregoing, it will be seen that the present invention provides a highly effective, adaptable and simple barrier for use with articulating joint replacement devices. The barrier comprises a biocompatible membrane and means of fixation or attachment to one component of a joint replacement device. The device is adaptable for use with various types of joint replacement devices and may be provided in a variety of different configurations to facilitate easy attachment. The device may be attached by suture or other mechanical means or by incorporating areas promoting tissue growth and attachment.

It will be obvious to those skilled in the art to make various changes, alterations and modifications to the invention described herein. The extent that these various changes, alterations and modifications do not depart from the spirit and scope of the appended claims, they are intended to be encompassed therein.

I claim:

1. A method of using a membrane with an artificial hip joint, said artificial hip joint being of the type having a socket implanted in an acetabulum and a femoral component having a head on a shaft which is secured in an opening in a medullary canal of a femur and which head and socket articulate with respect to one another, said method comprising:
   a) securing the membrane to the femoral component adjacent the head;
   b) extending the membrane to cover at least a portion of the opening in the medullary canal; and
   c) securing an edge of the membrane to adjacent tissue surrounding the opening in the medullary canal;

wherein the membrane comprises porous polytetrafluoroethylene and said membrane has opposing first and second surfaces and a thickness therebetween and said membrane is permeable to liquids through its thickness, said opposing first and second surfaces each having a mean pore size wherein the mean pore size of the first surface is substantially greater than the mean pore size of the second surface, and wherein the mean pore size of said first surface is in the range of about 10 to 40 microns and the mean pore size of the second surface is less than about 3 microns.

2. A method according to claim 1 wherein the mean pore size of the first surface is at least twice the mean pore size of the second surface.

3. A method according to claim 1 wherein said edge is secured by sutures.

4. A method of using a membrane with an artificial hip joint, said artificial hip joint being of the type having a socket implanted in an acetabulum and a femoral component having a head on a shaft which is secured in an opening in a medullary canal of a femur and which head and socket articulate with respect to one another, said method comprising:

a) securing the membrane to the femoral component adjacent the head;

b) extending the membrane to cover at least a portion of the opening in the medullary canal; and c) securing an edge of the membrane to adjacent tissue surrounding the opening in the medullary canal;

wherein the membrane comprises porous expanded PTFE having a microstructure of nodes and fibrils and said membrane has opposing first and second surfaces and a thickness therebetween and said membrane is permeable to liquids through its thickness, said opposing first and second surfaces each having a mean fibril length wherein the mean fibril length of the first surface is substantially greater than the mean fibril length of the second surface.

5. A method according to claim 4 wherein the mean fibril length of said first surface is in the range of about 10 to 40 microns and the mean fibril length of the second surface is less than about 3 microns.

6. A method according to claim 4 wherein the mean fibril length of the first surface is at least twice the mean fibril length of the second surface.

7. A method according to claim 4 wherein said edge is secured by sutures.

8. A method of using a membrane with an artificial joint implant, said joint implant having a component extending into an opening in a bone member, said method comprising:

a) securing the membrane to the artificial joint implant;

b) extending the membrane to cover at least a portion of the opening in the bone member; and c) securing an edge of the membrane to adjacent tissue surrounding the opening in the bone member;

wherein the membrane has opposing first and second surfaces and a thickness therebetween and said membrane is porous and permeable to liquids through its thickness, said opposing first and second surfaces each having a mean pore size wherein the mean pore size of the first surface is substantially greater than the mean pore size of the second surface, wherein the mean pore size of said first surface is in the range of about 10 to 40 microns and the mean pore size of the second surface is less than about 3 microns.

9. A method according to claim 8 wherein the mean pore size of the first surface is at least twice the mean pore size of the second surface.

10. A method according to claim 8 wherein said edge is secured by sutures.

11. A method according to claim 8 wherein said membrane comprises porous PTFE.

12. A method of using a membrane with an artificial hip joint, said artificial hip joint being of the type having a socket implanted in an acetabulum and a femoral component having a head on a shaft which is secured in an opening in a medullary canal of a femur and which head and socket articulate with respect to one another, said method comprising:

a) securing the membrane to the femoral component adjacent the head;

b) extending the membrane to cover at least a portion of the opening in the medullary canal; and c) securing an edge of the membrane to adjacent tissue surrounding the opening in the medullary canal;

wherein said membrane has opposing first and second surfaces and a thickness therebetween wherein said membrane is porous and permeable to liquids through its thickness, said membrane further having an intermediate layer disposed between said opposing first and second surfaces, each of said opposing first and second surfaces and said intermediate layer having a mean pore size wherein the mean pore size of the first surface and second surface is substantially greater than the mean pore size of the intermediate layer.

13. A method according to claim 12 wherein the mean pore size of said first and second surfaces is in the range of about 10 to 40 microns and the mean pore size of the intermediate layer is less than about 3 microns.

14. A method according to claim 12 wherein the mean pore size of the first and second surfaces is at least twice the mean pore size of the intermediate layer.

15. A method according to claim 12 wherein said edge is secured by sutures.

16. A method according to claim 12 wherein said membrane comprises porous PTFE.

17. A method according to claim 16 wherein the porous PTFE is porous expanded PTFE having a microstructure of nodes and fibrils.

* * * * *